(12) United States Patent
Elsheikh et al.

(10) Patent No.: US 10,022,576 B2
(45) Date of Patent: Jul. 17, 2018

(54) METHODS FOR PURIFYING AND STABILIZING HYDROFLUOROOLEFINS AND HYDROCHLOROFLUOROOLEFINS

(71) Applicant: Arkema Inc., King of Prussia, PA (US)

(72) Inventors: Maher Y. Elsheikh, Wayne, PA (US); Philippe Bonnet, Lyons (FR)

(73) Assignee: Arkema Inc., King of Prussia, PA (US)

( * ) Notice: Subject to any disclaimer, the term of this patent is extended or adjusted under 35 U.S.C. 154(b) by 136 days.

(21) Appl. No.: 14/773,775

(22) PCT Filed: Feb. 28, 2014

(86) PCT No.: PCT/US2014/019186
§ 371 (c)(1),
(2) Date: Sep. 9, 2015

(87) PCT Pub. No.: WO2014/158663
PCT Pub. Date: Oct. 2, 2014

(65) Prior Publication Data
US 2016/0023034 A1    Jan. 28, 2016

Related U.S. Application Data

(60) Provisional application No. 61/778,623, filed on Mar. 13, 2013.

(51) Int. Cl.
| | | |
|---|---|---|
| C09K 5/04 | (2006.01) | |
| A62D 1/00 | (2006.01) | |
| C07C 17/389 | (2006.01) | |
| C07C 17/42 | (2006.01) | |
| C09K 3/30 | (2006.01) | |
| C07C 21/18 | (2006.01) | |
| C08J 9/14 | (2006.01) | |
| C09K 3/00 | (2006.01) | |

(52) U.S. Cl.
CPC .......... *A62D 1/0092* (2013.01); *C07C 17/389* (2013.01); *C07C 17/42* (2013.01); *C07C 21/18* (2013.01); *C08J 9/146* (2013.01); *C09K 3/00* (2013.01); *C09K 3/30* (2013.01); *C09K 5/044* (2013.01); *C09K 5/045* (2013.01); *C08J 2300/22* (2013.01); *C09K 2205/126* (2013.01)

(58) Field of Classification Search
CPC .... C09K 2205/126; C09K 5/047; C09K 5/08; C09K 5/10; C10M 171/008; C10N 2030/12; C10N 2030/18; C10N 2040/30; C10N 2030/00; C10N 2030/06; C10N 2030/08; C10N 2030/10
USPC ...... 252/67, 68, 69, 2, 364; 264/41; 510/406
See application file for complete search history.

(56) References Cited

U.S. PATENT DOCUMENTS

| | | |
|---|---|---|
| 2,852,572 A | 9/1958 | Shukys et al. |
| 3,789,580 A | 2/1974 | Allemang et al. |
| 4,358,627 A | 11/1982 | Ameen et al. |
| 5,169,995 A | 12/1992 | Crooker et al. |
| 5,169,996 A | 12/1992 | Crooker et al. |
| 5,221,697 A | 6/1993 | Crooker et al. |
| 8,058,486 B2 * | 11/2011 | Merkel .................. C01B 7/035 570/135 |
| 8,388,857 B2 | 3/2013 | Elsheikh et al. |
| 8,691,107 B2 | 4/2014 | Elsheikh et al. |
| 9,650,551 B2 * | 5/2017 | Collier ..................... C09K 3/00 |
| 2003/0018225 A1 | 1/2003 | Klausmeyer |
| 2008/0045758 A1 | 2/2008 | Cohn et al. |
| 2008/0116417 A1 * | 5/2008 | Samuels ................. C07C 17/38 252/68 |
| 2009/0240090 A1 * | 9/2009 | Merkel .................. C01B 7/035 570/160 |
| 2010/0181524 A1 | 7/2010 | Elsheikh et al. |
| 2011/0105809 A1 | 5/2011 | Devic et al. |
| 2011/0196178 A1 | 8/2011 | Nyberg |
| 2011/0313215 A2 * | 12/2011 | Wendlinger ........... B01J 23/866 570/158 |
| 2011/0319675 A2 * | 12/2011 | Deur-Bert ............. C07C 17/087 570/153 |
| 2012/0203037 A1 * | 8/2012 | Sharratt ................ C07C 17/389 570/179 |
| 2012/0226081 A1 | 9/2012 | Elsheikh et al. |
| 2013/0105724 A1 * | 5/2013 | Boussand ............... C07C 21/18 252/68 |
| 2014/0066922 A1 | 3/2014 | Coe et al. |
| 2016/0230059 A1 * | 8/2016 | Takahashi ................ C11D 7/30 |
| 2017/0210962 A1 * | 7/2017 | Collier ..................... C09K 5/08 |

FOREIGN PATENT DOCUMENTS

| | | | |
|---|---|---|---|
| EP | 0309958 A2 | 4/1989 | |
| WO | WO 2007/144632 A1 | 12/2007 | |
| WO | WO 2008027515 A2 * | 3/2008 | ............. C09K 5/045 |
| WO | WO 2008027516 A1 * | 3/2008 | ............. C09K 5/045 |
| WO | WO 2008027596 A2 * | 3/2008 | ............. C09K 5/045 |
| WO | WO 2009/003165 A1 | 12/2008 | |
| WO | WO 2009/026526 A1 | 2/2009 | |

(Continued)

*Primary Examiner* — Douglas J McGinty
(74) *Attorney, Agent, or Firm* — Steven D. Boyd

(57) ABSTRACT

Hydrofluoroolefins and hydrochlorofluoroolefins contaminated with acid and/or iron compounds are purified and stabilized by contacting the haloolefin with a solid adsorbent such as alumina and then combining the purified haloolefin with one or more stabilizers such as an epoxide. The purified, stabilized haloolefins thus obtained are useful in a wide variety of end-use applications, including, for example, as refrigerants, propellants, foaming agents, fire suppression or extinguishing agents, and solvents.

23 Claims, No Drawings

(56) References Cited

FOREIGN PATENT DOCUMENTS

| WO | WO 2009/035893 A1 | 3/2009 | |
|---|---|---|---|
| WO | WO 2011/023923 A1 | 3/2011 | |
| WO | WO 2011/045559 A1 | 4/2011 | |
| WO | WO 2012004487 A2 * | 1/2012 | ............. C07C 21/18 |
| WO | WO 2014/060211 A1 | 4/2014 | |

* cited by examiner

METHODS FOR PURIFYING AND STABILIZING HYDROFLUOROOLEFINS AND HYDROCHLOROFLUOROOLEFINS

This present application is the national phase under 35 USC § 371 of prior PCT International Application Number PCT/US2014/019186 filed Feb. 28, 2014 which designated the United States of America and claimed priority to U.S. Provisional Patent Application Ser. No. 61/778,623 filed Mar. 13, 2013.

FIELD OF THE INVENTION

The invention relates to methods for purifying and stabilizing hydrofluoroolefins and hydrochlorofluoroolefins.

BACKGROUND OF THE RELATED ART

The Montreal Protocol for the protection of the ozone layer, signed in October 1987, mandates the phase-out of the use of chlorofluorocarbons (CFCs). Materials more "friendly" to the ozone layer, such as hydrofluorocarbons (HFCs), e.g., HFC-134a, replaced chlorofluorocarbons. However, these latter compounds have proven to be greenhouse gases capable of causing global warming and are now regulated by the Kyoto Protocol on Climate Change. The emerging replacement materials, hydrofluoropropenes, were shown to be environmentally acceptable, having zero ozone depletion potential (ODP) and low (much less than 150) global warming potential (GWP).

Currently proposed replacement refrigerants for hydrofluorocarbons such as HFC-134a include HFC-152a, pure hydrocarbons such as butane or propane, as well as "natural" refrigerants such as $CO_2$. Many of these suggested replacements are flammable and/or have low energy efficiency. Therefore, new alternative refrigerants are being sought. Fluoroolefin materials such as hydrofluoropropenes and/or hydrochlorofluoropropenes have generated interest as replacements for HFCs. The inherent chemical instability of these materials in the lower atmosphere provides the low global warming potential and zero or near zero ozone depletion properties desired. However, such inherent instability leads to degradation of such compounds during storage, handling and use in the presence of oxygen-containing substances such as air and water. Degradation generates acidic substances, which can result in the corrosion of equipment being used to store, handle or apply the fluoroolefins and which can catalyze further degradation.

SUMMARY OF THE INVENTION

The present invention provides a method comprising:
a) contacting an impure haloolefin composition comprised of a haloolefin selected from the group consisting of hydrofluoroolefins and hydrochlorofluoroolefins with a solid adsorbent to obtain a purified haloolefin composition; and
b) combining the purified haloolefin composition obtained from step a) with at least one stabilizer selected from the group consisting of free radical scavengers, oxygen scavengers, acid scavengers, water scavengers, polymerization inhibitors and corrosion inhibitors to obtain a purified, stabilized haloolefin composition.

Hydrofluoroolefins (HFOs) and hydrochlorofluoroolefins (HCFOs) produced in accordance with the invention thus may be stabilized during storage or shipping over an extended period of time, even though they are in contact with active metal materials (such as may be found in a shipping or storage container) and/or oxygen-containing substances which might normally lead to degradation of the haloolefin. The storage-stable HFOs and HCFOs obtained by practice of the invention are useful in end-use applications such as refrigeration, foam manufacturing, aerosol propellants and solvents.

Thus, one aspect of the invention provides a refrigeration, air-conditioning or heat pump system comprising a refrigerant, wherein the refrigerant comprises a purified, stabilized haloolefin composition prepared in accordance with the invention.

Another aspect of the invention provides a foamable polymer composition comprised of one or more polymer precursors or thermoplastic polymers and a blowing agent, wherein the blowing agent is comprised of a purified, stabilized haloolefin composition prepared in accordance with the invention.

Yet another aspect of the invention provides a sprayable composition comprised of at least one active ingredient and a propellant, wherein the propellant is comprised of a purified, stabilized haloolefin composition prepared in accordance with the invention.

A method of extinguishing or suppressing a fire is also provided by the invention, the method comprising discharging an agent comprised of a purified, stabilized haloolefin composition in accordance with the invention disposed in a pressured discharge system into an area to extinguish or suppress a fire in the area.

A method of inerting an area to prevent a fire or explosion is additionally provided by the invention, the method comprising discharging an agent comprised of a purified, stabilized haloolefin composition in accordance with the invention disposed in a pressured discharge system to prevent a fire or explosion from occurring.

Still another aspect of the invention provides a solution comprised of a substance and a solvent, wherein the solvent comprises a purified, stabilized haloolefin composition in accordance with the invention.

DETAILED DESCRIPTION OF THE INVENTION

The haloolefins useful in the present invention are olefin compounds containing a carbon-carbon double bond, at least one hydrogen atom and at least one fluorine atom per molecule, with chlorine atoms also optionally being present. The haloolefin may be non-cyclic or cyclic, branched or linear. Suitable open chain (non-cyclic) hydrofluoroolefins and/or hydrochlorofluoroolefins include $C_2$, $C_3$ and $C_4$ haloolefins of general formula $C_nH_{2n-a-b}F_aCl_b$, wherein n is 2, 3 or 4, b is 0 or 1, and a is 0 to 6 and a and b are not both 0. Suitable haloolefins also include $C_3$ to $C_5$ cyclic haloolefins of general formula $C_nH_{2(n-1)-a-b}F_aCl_b$, wherein n is 3 to 5, b is 0 or 1, and a is 0 to 7 and a and b are not both 0. Exemplary specific haloolefins include, but are not limited to, 1234yf, 1234ze, 1223xf, t-1233zd, 1243zf, 1233xf and 1336mzz. Individual haloolefins as well as mixtures of two or more different haloolefins may be treated in accordance with the methods of the present invention. The hydrofluoroolefins and/or hydrochlorofluoroolefins may exist as different configurational isomers or stereoisomers. The present invention is intended to include all single configurational isomers, single stereoisomers or any combination or mixture thereof. For instance, the designation 1,3,3,3-tetra-fluoropropene (HFC-1234ze) is meant to represent the cis-isomer, trans-isomer, or any combination or mixture of both isomers in any ratio. Another example is HFC-1225ye, by which is meant the cis-isomer, trans-isomer, or any combination or mixture of both isomers in any ratio.

The impure haloolefin composition utilized as a starting material may be obtained from any suitable source, including a commercial plant utilizing any of the conventional or known technologies for producing haloolefins. The process of the invention may be utilized to purify and stabilize an impure haloolefin composition directly after the haloolefin has been synthesized. Alternatively, the inventive process may be used to treat a haloolefin composition after it has been stored for some period of time under conditions effective to generate or accumulate impurities. Typically, the impure haloolefin composition will be contaminated with one or more impurities such as, for example, acids (e.g., HF, HCl, trifluoroacetic acid), aldehydes (e.g., trifluoroacetaldehyde) and/or iron compounds (e.g., $FeCl_3$). For example, impure haloolefin compositions suitable for treatment in accordance with the present invention may contain at least 50, at least 100, at least 250 or at least 500 ppm total acid and/or at least 1, at least 5 or at least 10 ppm $FeCl_3$.

Purification and stabilization of HFOs and/or HCFOs in accordance with the present invention involves a two step process. In a first step, absorption of impurities in the starting material (e.g., $FeCl_3$ and degradation products such as trifluoroacetic acid, trifluoroacetaldehyde, HF and HCl) is carried out using a solid adsorbent, such as activated carbon or a metal oxide such as high surface area (HAS) alumina. The adsorbent may, for example, have a surface area of 10-1000 $m^2/g$ and/or a pore volume of from 0.01-1 $cm^3/g$. The solid adsorbent advantageously has a very high capacity for adsorbing acids. For example, it may have the capability of removing greater than 90% or greater than 99% of the acid originally present in the HFO and/or HCFO. The adsorbent, before being contacted with the HFO and/or HCFO, may be subjected to a drying process, such as being placed under vacuum or heated (e.g., to 100-200° C., optionally under vacuum) until the desired level of dryness is attained.

The adsorption process can, for example, be carried out at any temperature between 0 and 100° C. (in one embodiment, at around room temperature, e.g., about 15-30° C.). The pressure during the adsorbent contacting step may be subatmospheric, atmospheric or high pressure (above atmospheric pressure). The HFO and/or HCFO may be contacted with the adsorbent while in liquid form, although alternatively the HFO or HCFO to be purified may be in gaseous form during such contacting step. The contact time when the HFO or HCFO is in liquid form may, for example, be between 0.1-5 minutes. When the HFO or HCFO is in gaseous form, the contact time with the adsorbent may suitably be 1-10 seconds. The starting material to be purified may be passed through a bed of the solid adsorbent. In another embodiment, the HFO or HCFO may be slurried or otherwise mixed or agitated with a portion of the solid adsorbent and then separated (by filtration, for example) from the solid adsorbent. The HFO or HCFO may be subjected to repeated absorbent contacting operations. For example, a stream of the starting material may be passed through a bed of the solid absorbent and the HFO or HCFO exiting the bed recycled and passed through the bed one or more additional times until the desired level of purity is attained. In one embodiment of the invention, the adsorbent contacting conditions are selected to provide a purified HFO and/or HCFO containing less than 1 ppm of total acid and less than 0.1 ppm of $FeCl_3$. The purified HFO and/or HCFO can be then be stored in a ferrous container and in the presence of an oxygen-containing gas, although generally it will be advantageous to first stabilize the purified product as described below.

In a second step, the purified HFO and/or HCFO is combined with at least one stabilizer selected from the group consisting of free radical scavengers, oxygen scavengers, acid scavengers, polymerization inhibitors and corrosion inhibitors. The amount of stabilizer employed is generally selected to be effective to impart the desired degree of stabilization to the composition. The stabilizer concentration can, for example, be varied from about 10 to about 2000 ppm or from about 100 to about 1500 ppm. Certain stabilizers may be capable of performing multiple functions; for example, a particular compound may act as both an acid scavenger and a corrosion inhibitor.

Suitable stabilizers for purposes of the present invention include, but are not limited to, hydroxylamines (e.g., diethylhydroxylamine), quinones (e.g., hydroquinone), oximes (e.g., methylethylketooxime), phenols (e.g., p-methoxyphenol), vinyl aromatic compounds (e.g., alpha-methyl styrene), epoxides (e.g., alpha-pinene oxide, beta-pinene oxide, 1,2-epoxybutane, 1,2-hexadecene oxide, glycidyl methyl ether, d,l-limonene oxide, alpha-glycidyl isopropylether, 1,2-epoxy-2-methylpropene), hydrazine, olefins such as d,l-limonene and isoprene, nitroalkanes (e.g., nitromethane, nitroethane), thionylchloride and the like and combinations thereof.

In the presence of such stabilizers, an HFO or HCFO product can be shipped or stored in a ferrous or other active metal-containing container in the presence of an oxygen-containing compound such as air or water for an extended period of time without the product exhibiting an unacceptable degree of decomposition.

In one embodiment of the invention, the purification and stabilization steps are carried out at the site of the initial production of the HFO or HCFO, prior to storage or transportation to the location where the purified, stabilized HFO or HCFO is to be used.

Purified, stabilized HFOs (e.g., 1234yf, t-1234ze, 1243zf) and HCFOs (e.g., t-1233zd, 1233xf) obtained in accordance with the present invention have utility, for example, in major applications such as: the manufacturing of XPS or PUR foam; refrigeration, as in MAC, chillers and heat pumps; and as solvents and aerosol propellants. Such products exhibit little or no degradation and little or no tendency to corrode the equipment they come into contact with during use, as discussed below.

Mobile Air Conditioning (MAC) Applications and Other Refrigerant Applications:

For MAC applications, the preferred boiling point (bp) of the low GWP refrigerants is between −10 to −40° C. Such a refrigerant must be chemically stable during use; e.g., the refrigerant doesn't react with active metal in the system such as aluminum and copper and it is soluble in and compatible with refrigerant oil.

The hydrofluoroolefins and/or hydrochlorofluoroolefins produced in accordance with the present invention have been found effective as replacements for high GWP (global warming potential) refrigerants in refrigeration, air-conditioning, and heat pump systems. Conventional high GWP refrigerants in such systems include materials such as R134a, R22, R245fa, R114, R236fa, R124, R410A, R407C, R417A, R422A, R507A, and R404A. The purified, stabilized hydrofluoroolefins and/or hydrochlorofluoroolefins of the present invention are effective working fluids in any refrigeration, air-conditioning, or heat pump apparatus that uses or is designed to use conventional high GWP refrigerants.

Vapor-compression refrigeration, air-conditioning, and heat pump systems include an evaporator, a compressor, a condenser, and an expansion device. A vapor-compression cycle re-uses refrigerant in multiple steps producing a cooling effect in one step and a heating effect in a different step. The cycle can be described simply as follows: liquid refrigerant enters an evaporator through an expansion device, and the liquid refrigerant boils in the evaporator at a low temperature to form a gas and produce cooling. The low-pressure gas enters a compressor where the gas is compressed to raise its pressure and temperature. The higher-pressure (compressed) gaseous refrigerant then enters the condenser in which the refrigerant condenses and discharges its heat to the environment. The refrigerant returns to the expansion device through which the liquid expands from the higher-pressure level in the condenser to the low-pressure level in the evaporator, thus repeating the cycle.

As used herein, mobile refrigeration apparatus or mobile air-conditioning (MAC) apparatus refers to any refrigeration or air-conditioning apparatus incorporated into a transportation unit for the road, rail, sea or air. The present invention is particularly useful for road transport refrigerating or air-conditioning apparatus, such as automobile air-conditioning apparatus or refrigerated road transport equipment.

The purified, stabilized HFO and/or HCFO of the present invention is also useful in stationary air-conditioning and heat pumps, e.g., chillers, high temperature heat pumps, residential and light commercial and commercial air-conditioning systems. In stationary refrigeration applications, the present compositions are useful in equipment such as domestic refrigerators, ice machines, walk-in and reach-in coolers and freezers, and supermarket systems.

When used as refrigerants, the hydrofluoroolefins and/or hydrochlorofluoroolefins of the present invention typically will be combined with refrigeration lubricants, i.e., those lubricants suitable for use with refrigeration, air-conditioning, or heat pump apparatus. Among these lubricants are those conventionally used in compression refrigeration apparatus utilizing chlorofluorocarbon refrigerants.

Such lubricants and their properties are discussed in the 1990 ASHRAE Handbook, Refrigeration Systems and Applications, chapter 8, titled "Lubricants In Refrigeration Systems". Lubricants useful in combination with the purified, stabilized products of the present invention may comprise those commonly known as "mineral oils" in the field of compression refrigeration lubrication. Mineral oils comprise paraffins (i.e., straight-chain and branched-chain, saturated hydrocarbons), naphthenes (i.e., cyclic paraffins) and aromatics (i.e., unsaturated, cyclic hydrocarbons containing one or more rings characterized by alternating double bonds). Lubricants useful with the purified, stabilized HFOs and HCFOs of the present invention further comprise those commonly known as "synthetic oils" in the field of compression refrigeration lubrication. Synthetic oils comprise alkylaryls (i.e., linear and branched alkyl alkylbenzenes), synthetic paraffins and napthenes, and poly(alpha-olefins). Suitable lubricants further comprise those that have been designed for use with hydrofluorocarbon refrigerants and are miscible with refrigerants of the present invention under compression refrigeration, air-conditioning, or heat pump apparatus operating conditions. Such lubricants include, but are not limited to, polyol esters (POEs) such as Castrol® 100 (Castrol, United Kingdom), polyalkylene glycols (PAGs) such as RL-488A from Dow (Dow Chemical, Midland, Mich.), and polyvinyl ethers (PVEs). Such lubricants are readily available from various commercial sources.

Lubricants for use in the present invention are selected by considering a given compressor's requirements and the environment to which the lubricant will be exposed. Commonly used refrigeration system stabilizers may optionally be added, as desired, to compositions of the present invention in order to enhance lubricity and system stability. These stabilizers are generally known within the field of refrigeration compressor lubrication, and include anti wear agents, extreme pressure lubricants, corrosion and oxidation inhibitors, metal surface deactivators, foaming and antifoam control agents, leak detectants and the like. In general, these stabilizers are present only in small amounts relative to the overall lubricant composition. They are typically used at concentrations of from less than about 0.1% to as much as about 3% by weight of each stabilizer. These stabilizers are selected on the basis of the individual system requirements. Some typical examples of such stabilizers may include, but are not limited to, lubrication enhancing stabilizers, such as alkyl or aryl esters of phosphoric acid and of thiophosphates. Additionally, metal dialkyl dithiophosphates and other members of this family of chemicals may be used in compositions of the present invention. Other antiwear stabilizers include natural product oils and asymmetrical polyhydroxyl lubrication stabilizers such as Synergol TMS (International Lubricants).

Blowing Agent Applications:

The purified, stabilized haloolefin compositions of the present invention are useful as blowing agents. For example, the haloolefin compositions may be employed to expand or foam polymeric systems, including both formulations is comprised of polymer precursors (i.e., monomers and/or oligomers capable of reacting to form a polymeric matrix, in particular a thermoset such as a polyurethane) as well as formulations comprised of one or more thermoplastic polymers.

For polyurethane blowing applications, the haloolefin composition typically is selected to have a boiling point between about −40° C. to about 30° C. and to be compatible with the A side, the B side or both. Typically, suitable haloolefin compositions are liquid at atmospheric pressure within the temperature range of from about 20° C. to 50° C. or from about 30° C. to about 40° C. and provide a foam with good dimensional stability. The halooefin compositions have a low thermal conductivity and provide a foam with low thermal conductivity.

For the production of thermoplastic foams, the stabilized, purified haloolefin compositions of the present invention may be selected to have a boiling point less than the melt and/or glass transition temperature of the polymer resin, typically less than about 100° C., preferably between about −40° C. to about 10° C. A process for preparing a foamed thermoplastic product may be as follows: Prepare a foamable polymer composition by blending together components comprising a foamable polymer composition in any order. Typically, a foamable polymer composition is prepared by plasticizing a polymer resin and then blending in components of a blowing agent composition (including a stabilized purified haloolefin composition in accordance with the present invention) at an initial pressure. A common process of plasticizing a polymer resin is heat plasticization, which involves heating a polymer resin to soften it sufficiently to blend in a blowing agent composition. Generally, heat plasticization involves heating a thermoplastic polymer resin near or above its glass transition temperature (Tg), or melt temperature (Tm) for crystalline polymers.

A foamable polymer composition can contain one or more additional stabilizers such as nucleating agents, cell-controlling agents, dyes, pigments, fillers, antioxidants, extrusion aids, stabilizing agents, antistatic agents, fire retardants, IR attenuating agents and thermally insulating stabilizers.

Nucleating agents include, among others, materials such as talc, calcium carbonate, sodium benzoate, and chemical blowing agents such azodicarbonamide or sodium bicarbonate and citric acid. IR attenuating agents and thermally insulating stabilizers include, for example, carbon black, graphite, silicon dioxide, metal flake or powder, among others. Flame retardants can include, among others, brominated materials such as hexabromocyclodecane and polybrominated biphenyl ether. Suitable foam preparation processes include batch, semi-batch, and continuous processes. Batch processes involve preparation of at least one portion of the foamable polymer composition in a storable state and then using that portion of foamable polymer composition at some future point in time to prepare a foam. A semi-batch process involves preparing at least a portion of a foamable polymer composition and intermittently expanding that foamable polymer composition into a foam all in a single process. For example, U.S. Pat. No. 4,323,528, herein incorporated by reference in its entirety for all purposes, discloses a process for making polyolefin foams via an accumulating extrusion process. The process comprises: 1) mixing a thermoplastic material and a blowing agent composition to form a foamable polymer composition; 2) extruding the foamable polymer composition into a holding zone maintained at a temperature and pressure which does not allow the foamable polymer composition to foam, wherein the holding zone has a die defining an orifice opening into a zone of lower pressure at which the foamable polymer composition foams and an openable gate closing the die orifice; 3) periodically opening the gate while substantially concurrently applying mechanical pressure by means of a movable ram on the foamable polymer composition to eject it from the holding zone through the die orifice into the zone of lower pressure and 4) allowing the ejected foamable polymer composition to expand to form the foam.

A continuous process involves forming a foamable polymer composition and then expanding that foamable polymer composition in a non-stop manner. For example, a foamable polymer composition may be prepared in an extruder by heating a polymer resin to form a molten resin, blending into the molten resin a blowing agent composition at an initial pressure to form a foamable polymer composition, and then extruding that foamable polymer composition through a die into a zone at a foaming pressure and allowing the foamable polymer composition to expand into a foam. Desirably, the foamable polymer composition is cooled after addition of the blowing agent and prior to extruding through the die in order to optimize foam properties. The foamable polymer composition may be cooled, for example, with heat exchangers.

Foams produced using a purified, stabilized haloolefin composition in accordance with the present invention can be of any form imaginable including sheet, plank, rod, tube, beads, or any combination thereof. For example, the foam may comprise a laminate foam that comprises multiple distinguishable longitudinal foam members that are bound to one another.

In another embodiment, the present invention relates to blowing agent compositions comprising the purified, stabilized hydrofluoroolefins and/or hydrochlorofluoroolefins as described herein, which are useful for use preparing foams. In other embodiments, the invention provides foamable compositions, such as polyurethane, polyisocyanate or thermoplastic foam compositions, comprised of a purified, stabilized haloolefin composition produced in accordance with the present invention, as well as methods of preparing foams from such foamable compositions. In such foam embodiments, one or more of the present HFO and/or HCFO compositions which has been purified and stabilized by addition of one or more stabilizers is included as a blowing agent in a foamable composition, which may also include one or more additional components capable of reacting and foaming under the proper conditions to form a foam or cellular structure. Any of the methods well known in the art may be used or adapted for use in accordance with the foam embodiments of the present invention.

The present invention further relates to a method of forming a foam comprising:
(a) combining a foamable composition with a purified, stabilized haloolefin composition in accordance with the present invention; and
(b) processing the foamable composition under conditions effective to form a foam.

Propellants:

Another embodiment of the present invention relates to the use of the purified, stabilized haloolefin compositions as described herein as propellants in sprayable compositions. Additionally, the present invention relates to a sprayable composition comprising at least one active ingredient and a purified, stabilized haloolefin composition prepared as described herein. The active ingredient(s) to be sprayed may be present in combination with one or more inert ingredients, solvents and other materials. Preferably, the sprayable composition is an aerosol. Suitable active materials to be sprayed include, without limitation, cosmetic materials, such as deodorants, perfumes, hair sprays, cleaners, and polishing agents as well as medicinal materials such as anti-asthma and anti-halitosis medications.

The present invention further relates to a process for producing an aerosol product comprising the step of combining a purified, stabilized haloolefin composition as described herein with one or more active ingredients in an aerosol container, wherein said composition functions as a propellant.

Fire Fighting Agents:

A further embodiment of the invention provides methods of extinguishing or suppressing a fire in a total-flood application comprising providing an agent comprising a purified, stabilized haloolefin composition in accordance with the present invention; disposing the agent in a pressurized discharge system; and discharging the agent into an area to extinguish or suppress fires in that area. Another embodiment provides methods of inerting an area to prevent a fire or explosion comprising providing an agent comprising a purified, stabilized haloolefin composition in accordance with the present invention; disposing the agent in a pressurized discharge system; and discharging the agent into the area to prevent a fire or explosion from occurring.

The term "extinguishment" is usually used to denote complete elimination of a fire; whereas, "suppression" is often used to denote reduction, but not necessarily total elimination, of a fire or explosion. As used herein, the terms "extinguishment" and "suppression" will be used interchangeably. There are four general types of halocarbon fire and explosion protection applications. In total-flood fire extinguishment and/or suppression applications, the agent is discharged into a space to achieve a concentration sufficient to extinguish or suppress an existing fire. Total flooding use includes protection of enclosed, potentially occupied spaces such as computer rooms as well as specialized, often unoccupied spaces such as aircraft engine nacelles and engine compartments in vehicles. In streaming applications, the agent is applied directly onto a fire or into the region of a fire. This is usually accomplished using manually operated wheeled or portable units. A second method, included as a streaming application, uses a "localized" system, which discharges agent toward a fire from one or more fixed nozzles. Localized systems may be activated either manually or automatically. In explosion suppression, the agent is discharged to suppress an explosion that has already been initiated. The term "suppression" is normally used in this application because the explosion is usually self-limiting. However, the use of this term does not necessarily imply that the explosion is not extinguished by the agent. In this application, a detector is usually used to detect an expanding fireball from an explosion, and the agent is discharged rapidly to suppress the explosion. Explosion suppression is used primarily, but not solely, in defense applications. In insertion, a purified, stabilized haloolefin in accordance with the present invention is discharged into a space to prevent an explosion or a fire from being initiated. Often, a system similar or identical to that used for total-flood fire extinguishment or suppression is used.

Usually, the presence of a dangerous condition (for example, dangerous concentrations of flammable or explosive gases) is detected, and the agent is then discharged to prevent the explosion or fire from occurring until the condition can be remedied.

The extinguishing method can be carried out by introducing a composition produced in accordance with the present invention into an enclosed area surrounding a fire. Any of the known methods of introduction can be utilized provided that appropriate quantities of the composition are metered into the enclosed area at appropriate intervals. For example, the purified, stabilized haloolefin composition can be introduced by streaming, e.g. using conventional portable (or fixed) fire extinguishing equipment; by misting; or by flooding, e.g., by releasing (using appropriate piping, valves, and controls) the composition into an enclosed area surrounding a fire. The composition can optionally be combined with an inert propellant, e.g., nitrogen, argon, decomposition products of glycidyl azide polymers or carbon dioxide, to increase the rate of discharge of the composition from the streaming or flooding equipment utilized.

In one embodiment, the extinguishing process involves introducing a purified, stabilized haloolefin composition produced in accordance with the present invention to a fire or flame in an amount sufficient to extinguish the fire or flame. One skilled in this field will recognize that the amount of flame suppressant needed to extinguish a particular fire will depend upon the nature and extent of the hazard. When the flame suppressant is to be introduced by flooding, cup burner test data is useful in determining the amount or concentration of flame suppressant required to extinguish a particular type and size of fire.

Solvent:

The purified, stabilized haloolefin compositions of the present invention are useful as solvents, wherein one or more substances are dissolved in the haloolefin composition to provide a solution. A hydrochlorofluoroolefin and/or hydrofluoroolefin suitable for solvent applications typically is selected to have a boiling point at atmospheric pressure of 18-60° C. The haloolefin product should be chemically stable in contact with metals and not cause swelling when brought into contact with various plastics such as acrylonitrile butadiene styrene, PVC, polybutylene terephthalate, polyethylene HD, polyethylene LD, polymethyl methacrylate, polyethylene, high impact polystyrene, polystyrene crystals, polystyrene 1160, polypropylene, polyamide 11, polycarbonate, polyvinylidene fluoride, and polyether block amide; or elastomeric materials such as styrene butadiene rubber, ethylene propylene rubber, hydrogenated nitrile rubber, polychloroprene, polyacrylate rubbers, hypalon rubbers, fluorocarbon df, nitrile rubbers, silicone elastomers, polyisoprene, and polybutadiene. Useful solvent applications include, but are not limited to, the utilization of the haloolefin product as a defluxing agent, to remove oils or other residues from surfaces, and to deposit or remove lubricants onto or from surfaces.

EXAMPLES

Example 1

Purification of Commercial 1234yf by Contact with Activated Alumina

In this example, a commercial sample of 1234yf, containing 150 ppm of trifluoroacetic acid and 200 ppm of HF, as quantitatively determined by ion chromatography (IC), was fed over 85 g of Engelhard 4028 alumina, which had been previously activated by heating at 150° C. for approximately 4 hours. The dry activated alumina had a surface area of 223 $m^2$/g and a pore volume of 0.49 g/cc, at 22° C., at a rate of 20 cc/m. The contact time was about 5.3 minutes. Analysis of the purified 1234yf found less than 5 ppm of trifluoroacetic acid and less than 5 ppm of HF by IC.

Example 2

Accelerated Aging Test of Acid-Free 1234yf

The acid-free 1234yf obtained from Example 1 was placed in an aerosol bottle. The bottle was capped in the presence of air and aged at 50° C. for 18 hours, in the presence of a metal coupon selected from Cu, 304SS, and Al. Analysis of the 1234yf by IC showed less than 5 ppm trifluoroacetic acid and HF. Visual inspection of the metal coupon found no evidence of corrosion or discolorations.

Example 3

Stabilization of Commercial 1234yf by the Addition of Inhibitors

Impure 1234yf (20 grams) containing trifluoroacetic acid (150 ppm) and HF (200 ppm) was placed in a 50 cc aerosol glass bottle in combination with 500 ppm of α-methyl styrene. The same procedure was repeated with an additional five bottles, each containing 500 ppm of one of the following inhibitors: 1,2-epoxy butane, α-pinene oxide, β-pinene oxide, hexadecene oxide, and α-glycidyl isopropyl ether. After aging at 50° C. for 18 hours, IC analysis showed no increase in the level of trifluoroacetic acid or HF in any of the samples.

Example 4

Stabilization of Commercial Grade t-1233zd by Contact with Activated Alumina

Commercially produced t-1233zd, containing low levels of impurities such as trifluoroacetic acid, HF and HCl (each was present at a concentration of approximately 200 ppm), was purified by contact with commercial alumina, such as was used in Example 1. Analysis of the purified t-1233zd found that the level for each of the three acids was less than 5 ppm. The acid-free t-1233zd was subjected to an accelerated aging test in an aerosol bottle in the presence of an active metal coupon such as a Cu, Fe or Al coupon. After heating at 50° C. for 18 hours, analysis of the product showed no increase in the level of the three acids. Additionally, there was no evidence of metal corrosion or discoloration.

Example 5

Stabilization of Commercial Grade t-1233zd by Addition of Inhibitor

Into each of five different 50 cc aerosol bottles was placed 20 g of commercial HFO t-1233zd containing impurities such as trifluoroacetic acid (180 ppm), HCl (220 ppm), and HF (200 ppm). Each bottle also contained 1000 ppm of an inhibitor (α-methyl styrene, 1,2-epoxy butane, α-pinene oxide, β-pinene oxide, hexadecene oxide, α-glycidyl isopropyl ether). The aerosol bottles were then capped in the presence of air. After aging at 50° C. for 18 hours, acid analysis by IC showed no increase in the concentration of trifluoroacetic acid, HCl or HF

What is claimed is:

1. A method comprising:
   a) contacting an impure haloolefin composition comprised of a haloolefin selected from the group consisting of hydrofluoroolefins and hydrochlorofluoroolefins containing impurities selected from the group consisting of acids, aldehydes, iron compounds, their degradation products and mixtures thereof with a solid adsorbent to obtain a purified haloolefin composition whereby said impurities have been removed; and
   b) combining the purified haloolefin composition obtained from step a) with at least one stabilizer selected from the group consisting of free radical scavengers, oxygen scavengers, acid scavengers, polymerization inhibitors and corrosion inhibitors to obtain a purified, stabilized haloolefin composition.

2. The method of claim 1, wherein the impure haloolefin composition comprises one or more impurities selected from the group consisting of $FeCl_3$, trifluoroacetic acid, trifluoroacetaldehyde, HF and HCl.

3. The method of claim 1, wherein the solid adsorbent is selected from the group consisting of high surface area alumina, activated carbon and mixtures thereof.

4. The method of claim 1, wherein the haloolefin is an open chain haloolefin of general formula $C_nH_{2n-a-b}F_aCl_b$, wherein n is 2, 3 or 4, b is 0 or 1, and a is 0 to 6 and a and b are not both 0.

5. The method of claim 1, wherein the haloolefin is a $C_3$ to $C_5$ cyclic hydrochlorofluoroolefin of general formula $C_nH_{2(n-1)a-b}F_aCl_b$, wherein n is 3 to 5, b is 0 or 1, and a is 0 to 7 and a and b are not both 0.

6. The method of claim 1, wherein the haloolefin is selected from the group consisting of 1234yf, 1234ze, 1223xf, t-1233zd, 1243zf, 1233xf and 1336mzz.

7. The method of claim 1, comprising a further step of placing the purified, stabilized haloolefin composition in a container in contact with an active metal.

8. The method of claim 1, comprising a further step of admixing the purified, stabilized haloolefin composition with an oxygen-containing compound.

9. The method of claim 1, wherein the solid adsorbent is capable of adsorbing acid.

10. The method of claim 1, wherein the solid adsorbent is an activated alumina having a surface area of 100 to 1000 $m^2/g$ and a pore volume of 0.1 to 1 $cm^3/g$.

11. The method of claim 1, wherein the solid adsorbent has a surface area of 10 to 1000 $m^2/g$ and a pore volume of 0.01 to 1 $cm^3/g$.

12. The method of claim 1, wherein the stabilizer includes an epoxide.

13. The method of claim 1, wherein the stabilizer includes at least one of α-methyl styrene, 1,2-epoxy butane, α-pinene oxide, β-pinene oxide, hexadecene oxide, or α-glycidyl isopropyl ether.

14. The method of claim 1, wherein the stabilizer is selected from the group consisting of hydroxylamines, quinones, oximes, phenols, vinyl aromatic compounds, epoxides, hydrazine, olefins, nitroalkanes, thionylchloride and combinations thereof.

15. The method of claim 1, wherein the purified haloolefin composition is combined with from about 100 to about 1500 ppm stabilizer.

16. A purified, stabilized haloolefin composition produced in accordance with the method of claim 1.

17. A refrigeration, air-conditioning or heat pump system comprising a refrigerant, wherein the refrigerant comprises a purified, stabilized haloolefin composition in accordance with claim 16.

18. The refrigeration, air-conditioning or heat pump system of claim 17, wherein the refrigerant is additionally comprised of a lubricant.

19. A foamable polymer composition comprised of one or more polymer precursors or thermoplastic polymers and a blowing agent, wherein the blowing agent is comprised of a purified, stabilized haloolefin composition in accordance with claim 16.

20. A sprayable composition comprised of at least one active ingredient and a propellant, wherein the propellant is comprised of a purified, stabilized haloolefin composition in accordance with claim 16.

21. A method of extinguishing or suppressing a fire, comprising discharging an agent comprised of a purified, stabilized haloolefin composition in accordance with claim 16 disposed in a pressured discharge system into an area to extinguish or suppress a fire in the area.

22. A method of inerting an area to prevent a fire or explosion, comprising discharging an agent comprised of a purified, stabilized haloolefin composition in accordance with claim 16 disposed in a pressured discharge system to prevent a fire or explosion from occurring.

23. A solution comprised of a substance and a solvent, wherein the solvent comprises a purified, stabilized haloolefin composition in accordance with claim 16.

* * * * *